United States Patent [19]
Etzbach et al.

[11] Patent Number: 6,048,968
[45] Date of Patent: Apr. 11, 2000

[54] CATIONIC AZO DYES BASED ON AMINOBENZOIC ACID

[75] Inventors: Karl-Heinz Etzbach, Frankenthal; Torsten Freund, Limburgerhof; Rainer Tresch, Maxdorf, all of Germany

[73] Assignee: BASF Aktiengesellschaft, Ludwigshafen, Germany

[21] Appl. No.: 09/305,279

[22] Filed: May 5, 1999

[30] Foreign Application Priority Data

May 7, 1998 [DE] Germany .................. 198 20 400

[51] Int. Cl.[7] .......................... C09B 44/02; C09B 67/22; C09B 35/21; C07C 229/56; C07C 237/34
[52] U.S. Cl. .................. 534/604; 534/606; 534/614; 8/639; 560/36; 564/156
[58] Field of Search .................. 534/614, 604, 534/606; 8/639; 560/36; 564/156

[56] References Cited

U.S. PATENT DOCUMENTS

| | | | |
|---|---|---|---|
| 4,656,256 | 4/1987 | Colberg et al. | 534/605 |
| 5,117,058 | 5/1992 | Chem et al. | 564/156 X |

FOREIGN PATENT DOCUMENTS

| | | |
|---|---|---|
| 0 159 549 | 10/1985 | European Pat. Off. . |
| 0 162 409 | 11/1985 | European Pat. Off. . |
| 38 21 627 | 1/1989 | Germany . |

*Primary Examiner*—Fiona T. Powers
*Attorney, Agent, or Firm*—Oblon, Spivak, McClelland, Maier & Neustadt, P.C.

[57] ABSTRACT

Cationic azo dyes of the formula I

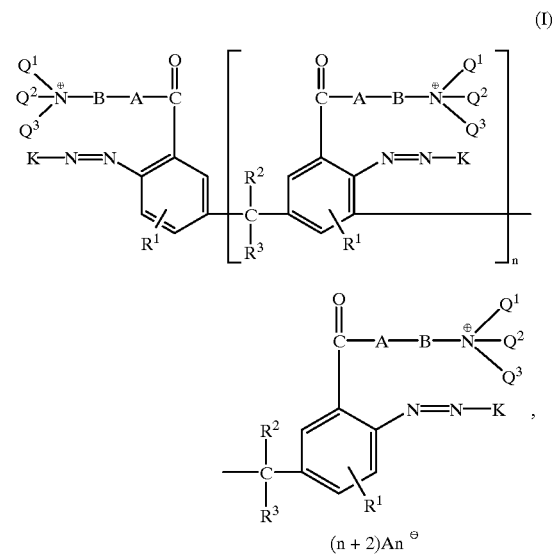

where the variables are as defined in the specification, amines as their intermediates, processes for preparing them, their use for dyeing and printing natural or synthtic substrates, and their mixtures are described.

10 Claims, No Drawings

CATIONIC AZO DYES BASED ON AMINOBENZOIC ACID

The present invention relates to novel cationic azo dyes of the formula I

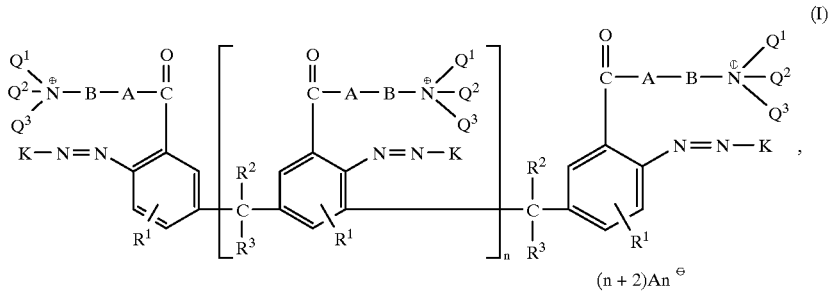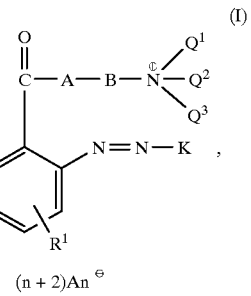 (I)

$(n + 2)An^{\ominus}$ where
- n is a number from 0 to 8,
- $R^1$ is hydrogen, nitro, halogen or $C_1$–$C_6$-alkyl,
- $R^2$ and $R^3$ independently are hydrogen or $C_1$–$C_6$-alkyl or together with the carbon atom linking them are a cyclopentyl or cyclohexyl radical,
- K is the radical of a coupling component,
- A is oxy, imino or unsubstituted or substituted $C_1$–$C_6$-alkylimino,
- B is $C_1$–$C_6$-alkylene which can be interrupted by 1 or 2 nonadjacent oxy, imino or unsubstituted or substituted $C_1$–$C_6$-alkylimino groups and a radical

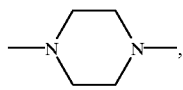

- $Q^1$, $Q^2$ and $Q^3$ independently are hydrogen, $C_1$–$C_{10}$-alkyl which can be interrupted by from 1 to 4 nonadjacent oxy, imino and unsubstituted or substituted $C_1$–$C_4$-alkylimino groups and can be substituted by hydroxyl, halogen or phenyl, and $Q^1$ and $Q^2$ together with the nitrogen atom linking them are a 5- or 6-membered heterocyclic radical with or without nitrogen or oxygen as a further heteroatom, and
- $An^{\ominus}$ is the equivalent of an anion, too amines as their intermediates, to a process for preparing them, to their use for dyeing and printing natural or synthetic substrates, and to their mixtures.

EP-A-0 162 409 describes basic azo dyes obtained by single or double coupling of alkyl anthranilates whose alkyl radical is alkylamino-substituted to resorcinol. In their use as paper dyes, however, these dyes exhibit deficiencies in affinity and color strength.

It is an object of the present invention to provide novel dyes which feature advantageous performance properties, in particular good light fastness properties, and also high color strength and fiber affinity. The dyed fibers should also have good fastness properties with respect to bleaches.

We have found that this object is achieved by the dyes of the formula I identified at the outset.

All alkyl or alkylene groups in the abovementioned formula can be either straight-chain or branched.

If substituted alkyl groups appear in the above formula, examples of suitable substituents are hydroxyl and methoxy. In that case the alkyl groups generally have 1 or 2 substituents.

If the radicals $Q^1$ and $Q^2$ together with the nitrogen atom linking them are a 5- or 6-membered heterocyclic radical with or without nitrogen or oxygen as a further heteroatom, suitable radicals may be saturated radicals such as pyrrolidinyl, piperidinyl, morpholinyl and piperazinyl, which can be substituted on the nitrogen by methyl, ethyl, propyl, isopropyl, n-, iso- and sec-butyl, 2-hydroxyethyl or 2- or 3-hydroxypropyl. Unsaturated radicals such as pyrrolyl, pyrazolyl, oxazolyl, isooxazolyl or imidazolyl, which may be substituted in positions 2 and/or 4 by methyl, ethyl, propyl or butyl, or N-3-($C_1$–$C_4$-alkyl)imidazolyl, which may be substituted in positions 2 and/or 4 by methyl, ethyl, propyl or butyl, may also be suitable.

Halogen radicals are fluorine, chlorine or bromine.

Radicals $R^1$, $R^2$, $R^3$, $Q^1$, $Q^2$ and $Q^3$ are, for example, methyl, ethyl, propyl, isopropyl, butyl, isobutyl, sec-butyl, tert-butyl, pentyl, isopentyl, neopentyl, tert-pentyl, hexyl or 2-methylpentyl.

Radicals $Q^1$, $Q^2$ and $Q^3$ are additionally, for example, heptyl, octyl, 2-ethylhexyl, isooctyl, nonyl, isononyl, decyl (the above designations isooctyl, isononyl and isodecyl are trivial names and derived from the alcohols obtained by oxo synthesis—cf. Ullmanns Encyklopädie der technischen Chemie, 4th Edition, Volume 7, pages 215 to 217, and Volume 11, pages 435 and 436), 2-hydroxyethyl, 2- or 3-hydroxypropyl, 2- or 4-hydroxybutyl, 2-chloroethyl, 2- or 3-chloropropyl, 2- or 4-chlorobutyl, benzyl, 1- or 2-phenylethyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6, 9-trioxaundecyl, 3,6,9-trioxadodecyl, 3,6,9,12-tetraoxatridecyl, 3,6,9,12-tetraoxatetradecyl, 4-hydroxy-2-methyl-3-azabutyl, 4-hydroxy-3-hydroxymethyl-2-methyl-3-azabutyl, 5-hydroxy-2-methyl-3-azapentyl, 5-hydroxy-3-(2-hydroxyethyl)-2-methyl-3-azapentyl, 8-hydroxy-2-methyl-3-aza-6-oxaoctyl, 11-hydroxy-2-methyl-3-aza-6,9-dioxaundecyl, 8-hydroxy-(5-hydroxy-3-oxapentyl)-2-methyl-3-aza-6-oxaoctyl or 11-hydroxy-3-(8-hydroxy-3,6-dioxaoctyl)-2-methyl-3-aza-6,9-dioxaundecyl, N,N-dimethylaminoethyl, N,N-diethylaminoethyl, N,N-dipropylaminoethyl, N,N-dibutylaminoethyl, 3-(N,N-dimethylamino)propyl, 3- (N,N-diethylamino)propyl, 3-(N, N-dipropylamino)propyl or 3-(N,N-dibutylamino)propyl.

Radicals A are, for example, methylimino, ethylimino, propylimino, isopropylimino, butylimino, isobutylimino, sec-butylimino, tert-butylimino, pentylimino, isopentylimino, neopentylimino, tert-pentylimino, hexylimino or 2-methylpentylimino.

Radicals B are, for example, methylene, ethylene, 1,2- or 1,3-propylene, 1,2-, 2,3- or 1,4-butylene, $(CH_2)_2O(CH_2)_2$, $(CH_2)_3O(CH_2)_2$, $(CH_2)_3O(CH_2)_3$, $(CH_2)_2O(CH_2)_2O(CH_2)_2$, $(CH_2)_2NH(CH_2)_2$, $(CH_2)_3NH(CH_2)_2$, $(CH_2)_2NH(CH_2)_2NH(CH_2)_2$,

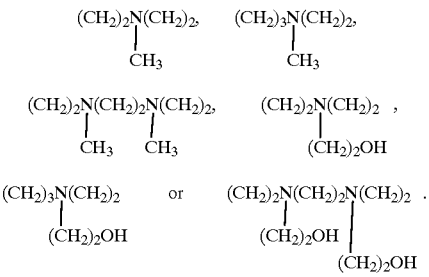

The equivalent $An^{\ominus}$ of an anion is derived, for example, from the following anions: fluoride, chloride, bromide, iodide, sulfate, phosphate, formate, acetate, propionate, mono-, di- or trichloroacetate, lactate, methoxyacetate, citrate, succinate, methanesulfonate, benzenesulfonate, 2- or 4-methylbenzenesulfonate or naphthalenesulfonate.

Suitable coupling components KH are compounds from the benzene, naphthalene, quinoline, pyridone, barbituric acid or pyrazolone series and correspond, for example, to the compounds of the formula II a–f

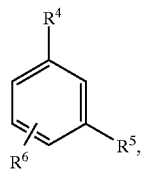 (IIa)

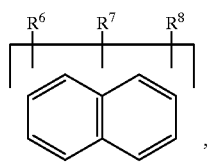 (IIb)

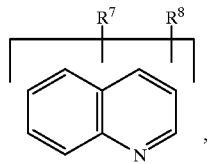 (IIc)

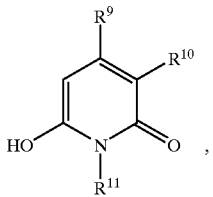 (IId)

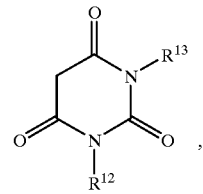 (IIe)

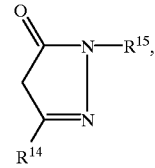 (IIf)

where
- $R^4$ is hydroxyl, amino, morpholino, mono- or di-$(C_1-C_6)$-alkylamino whose alkyl radicals are unsubstituted or substituted by hydroxyl, amino, cyano, $C_1-C_6$-alkoxycarbonyl, carbamoyl or mono- or di-$(C_1-C_6)$-alkylcarbamoyl and are uninterrupted or interrupted by oxy, or is $C_1-C_6$-alkoxy,
- $R^5$ is hydrogen, $C_1-C_6$-alkyl or a radical $R^4$,
- $R^6$ is hydrogen, $C_1-C_6$-alkyl, $C_1-C_6$-alkoxy whose alkyl radical is uninterrupted or interrupted by oxy, mono-or di-$(C_1-C_6$-alkyl)imino, $C_1-C6$-alkoxycarbonyl, carbamoyl, mono- or di-$(C_1-C_6$-alkyl)carbamoyl whose alkyl radicals are unsubstituted or substituted by hydroxyl or amino and uninterrupted or interrupted by oxy, or is sulfamoyl, mono- or di-$(C_1-C_6$-alkyl)sulfamoyl whose alkyl radicals are unsubstituted or substituted by hydroxyl or amino and are uninterrupted or interrupted by oxy, or is carboxyl,
- $R^7$ is hydroxyl, amino, mono- or di-$(C_1-C_{12}$-alkyl)amino or cyclohexylamino,
- $R^8$ is hydrogen, hydroxyl, amino, formylamino, acetylamino or $C_1-C_6$-alkyl,
- $R^9$ is hydrogen, $C_1-C_6$-alkyl, phenyl, hydroxyl, cyano, acetyl, benzoyl, methoxycarbonyl or carbamoyl,
- $R^{10}$ is hydrogen, chlorine, bromine, acetylamino, amino, nitro, sulfamoyl, methylsulfonyl, phenylsulfonyl, $C_1-C_4$-alkoxycarbonyl, $C_1-C_4$-alkanoyl, benzoyl, carbamoyl, cyano, N-methylimidazolyl or pyridinio,
- $R^{11}$ is hydrogen, $C_1-C_6$-alkyl which can be substituted by phenyl, hydroxyl, amino, $C_1-C_6$-alkoxyl, acetylamino, benzoylamino or cyano, or is cyclohexyl, phenyl which can be substituted by benzoylamino, acetylamino, methyl, methoxy, cyano or chloro, or is amino which is substituted by phenyl, $C_1-C_6$-alkyl, $C_1-C_6$-alkanoyl or benzoyl,
- $R^{12}$ or $R^{13}$ independently is hydrogen or $C_1-C_6$-alkyl,
- $R^{14}$ is methyl, $C_1-C_4$-alkoxycarbonyl or phenyl,
- $R^{15}$ is hydrogen, $C_1-C_6$-alkyl, cyclohexyl, benzyl or phenyl which is unsubstituted or substituted from one to three times by fluorine, chlorine, bromine, $C_1-C_4$-alkyl, $C_1-C_4$-alkoxy, cyano, acetyl, acetylamino, hydroxyl, sulfamoyl or carbamoyl.

Radicals $R^4$, $R^6$ and $R^7$ are, for example, mono- or dimethylamino, mono- or diethylamino, mono- or dipropylamino, mono- or diisopropylamino, mono- or dibutylamino, mono- or dipentylamino, mono- or diisopentylamino, mono- or dineopentylamino, mono- or dihexylamino, mono- or di-2-methylpentylamino, N-methyl-n-butylamino, and N-ethyl-n-butylamino.

Radicals $R^4$ are in addition, for example, mono- or di-(2-hydroxyethyl)amino, mono- or di-(2-hydroxypropyl)amino, mono- or di-(3-hydroxypropyl)amino, N-methyl-2-hydroxyethylamino, N-methyl-2-hydroxypropylamino, N-methyl-3-hydroxypropylamino, N-ethyl-2-hydroxyethylamino, N-ethyl-2-hydroxypropylamino, N-ethyl-3-hydroxypropylamino, N-propyl-2-hydroxyethylamino, N-propyl-2-hydroxypropylamino, N-propyl-3-hydroxypropylamino, N-isopropyl-2-hydroxyethylamino, -2-hydroxypropylamino, -3-hydroxypropylamino, mono- or di-(2-aminoethyl)amino, mono- or di-(2-aminopropyl)amino, mono- or di-(3-aminopropyl)amino, mono- or di-(2-aminobutyl)amino, mono- or di-(4-aminobutyl)amino, 2-cyanoethylamino, 2-cyano-2-methylethylamino, 2-methoxycarbonylethylamino, 2-methoxycarbonyl-2-methylethylamino, 2-ethoxycarbonylethylamino, 2-ethoxycarbonyl-2-methylethylamino, 2-propoxycarbonylethylamino, 2-propoxycarbonyl-2-methylethylamino, 2-isopropoxycarbonylethylamino, 2-isopropoxycarbonyl-2,-methylethylamino, 2-butoxycarbonylethylamino, 2-butoxycarbonyl-2-methylethylamino, 2-carbamoylethylamino, 2-carbamoyl-2-methylethylamino, 2-mono- or dimethylaminocarbonylethylamino, 2-mono- or dimethylaminocarbonyl-2-methylethylamino, mono- or di-(2-methoxyethyl)amino, mono- or di-(2-methoxypropyl)amino, mono- or di-(3-methoxypropyl)amino, or mono- or di-(2-hydroxyethyloxyethyl)amino.

Radicals $R^5$, $R^6$, $R^8$, $R^9$, $R^{11}$, $R^{12}$, $R^{13}$ and $R^{15}$ are, for example, methyl, ethyl, propyl, isopropyl, butyl, isobutyl, sec-butyl, tert-butyl, pentyl, isopentyl, neopentyl, tert-pentyl, hexyl or 2-methylpentyl.

The radicals $R^{11}$ are hydroxy-$C_1$–$C_4$-alkyl such as hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxy-prop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl, 2-hydroxymethylprop-2-yl, cyanomethyl, cyanoethyl, cyanopropyl or cyanobutyl.

Radicals $R^{11}$ are in addition, for example, benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)-eth-1-yl, 1-(phenylmethyl)prop-1-yl, preferably benzyl and 2-phenylethyl, methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methoxyethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl.

Radicals $R^{10}$ are, for example, formyl, acetyl, propionyl, butyryl or isobutyryl.

The radicals $R^6$ are, for example, mono- or dimethylcarbamoyl, mono- or diethylcarbamoyl, mono- or dipropylcarbamoyl, mono- or dibutylcarbamoyl, mono- or dipentylcarbamoyl or mono- or dihexylcarbamoyl.

Radicals $R^4$ and $R^6$ can, for example, be methoxy, ethoxy, propoxy, isopropoxy, butoxy, sec-butoxy, isobutoxy or tert-butoxy.

Radicals $R^6$ are in addition, for example, methoxyethyloxy, methoxypropyloxy, ethoxyethyloxy, ethoxypropyloxy or propoxypropyloxy.

Radicals $R^{15}$ are, for example, 2-, 3- or 4-fluorophenyl, 2-, 3- or 4-chlorophenyl, 2-, 3- or 4-bromophenyl, 2-, 3- or 4-methylphenyl, 2-, 3- or 4-ethylphenyl, 2-, 3- or 4-methoxyphenyl, 2-, 3- or 4-cyanophenyl, 2-, 3- or 4-hydroxyphenyl, 2-, 3- or 4-acetylphenyl, 2-, 3- or 4-acetylaminophenyl, 2-, 3- or 4-sulfamoylphenyl or 2-, 3- or 4-carbamoylphenyl.

The radicals $R^6$, $R^{10}$ and $R^{14}$ are, furthermore, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, isopentoxycarbonyl, neopentoxycarbonyl, tert-pentyloxycarbonyl, hexyloxycarbonyl or 2-methylpentyloxycarbonyl.

The radicals $R^6$ are additionally, for example, mono- or dimethylsulfamoyl, mono- or diethylsulfamoyl, mono- or dipropylsulfamoyl, mono- or dibutylsulfamoyl.

Examples of further suitable radicals $R^{11}$ are aminomethyl, 2-aminoethyl, 2- or 3-aminopropyl, 2- or 4-aminobutyl, acetylaminomethyl, 2-acetylaminoethyl, 2- or 3-acetylaminopropyl, 2- or 4-acetylaminobutyl, benzoylaminomethyl, 2-benzoylaminoethyl, 2- or 3-benzoylaminopropyl, 2- or 4-benzoylaminobutyl, 2-, 3- or 4-benzoylaminophenyl, 2-, 3- or 4-acetylaminophenyl, 2-, 3- or 4-methylphenyl, 2-, 3- or 4-methoxyphenyl, 2-, 3- or 4-cyanophenyl, 2-, 3- or 4-chlorophenyl, phenylamino, methylamino, ethylamino, propylamino, isopropylamino, butylamino, isobutylamino, sec-butylamino, tert-butylamino, acetylamino, propionylamino, butyrylamino, isobutyrylamino, valerylamino, isovalerylamino, pivaloyl, pentylcarbonyl or benzoylamino.

In the text below, coupling components KH are listed by way of example. Examples of coupling components of the benzene series are resorcinol, 2- and 4-methylresorcinol, 1,3-phenylenediamine, 3-aminophenol, 4-methyl-3-aminophenol, 5-amino-2-methylphenol, 4-ethyl-3-aminophenol, 3-N,N-diethylaminophenol, 2,4-diaminotoluene, 2,4-dihydroxybenzoic acid, 4-methyl-2-aminophenol, 3-acetaminophenol, 3-amino-4-hydroxybenzenesulfonamide, o-, m- or p-toluidine, o-, m- or p-xylidine, 2,5-dimethoxyaniline, 2-methoxy-5-methylaniline, 3-amino-4-methylacetanilide, 2- or 4-methoxyacetanilide, N-methylaniline, N-methyl-m- toluidine, N-ethylaniline, N,N-diethylaniline, E-ethyl-m-toluidine, N-(2-hydroxyethyl)aniline, N,N-dihydroxyethylaniline or N-(2-hydroxyethyl)-m-toluidine.

Examples of coupling components of the naphthalene series are 1-naphthylamine, N-phenyl-1-naphthylamine, N-ethyl-1-naphthylamine, N-ethyl-2-naphthylamine, N-phenyl-2-naphthylamine, 1-naphthol, 2-naphthol, 2,5-dihydroxynaphthalene, 1,6-dihydroxynaphthalene, 1,7-dihydroxynaphthalene, 2,7-dihydroxynaphthalene, 2-hydroxynaphthalene-1-carboxylic acid, 2-hydroxynaphthalene-3-carboxylic acid, methyl 2-hydroxynaphthalene-3-carboxylate or 2-hydroxynaphthalene-3-carboxylamide.

Examples of coupling components of the quinoline series are 8-hydroxyquinoline, 8-hydroxy-2-methylqiunoline, 8-aminoquinoline, 8-amino-2-methylquinoline, 2-hydroxyquinoline and 2,4-dihydroxyquinoline.

Examples of pyridone coupling components are 1-ethyl-2-hydroxy-4-methyl-5-carbamoylpyrid-6-one, 1-(2'-hydroxyethyl)2-hydroxy-4-methyl-5-carbamoylpyrid-6-one, 1-phenyl-2-hydroxy-4-methyl-5-carbamoylypyrid-6-one, 1-ethyl-2-hydroxy-4-methyl-5-cyanopyrid-6-one, 1-methyl-2-hydroxy-4-methyl-5-cyanopyrid-6-one, 1-methyl-2-hydroxy-5-acetylpyrid-6-one, 1,4-dimethyl-2-hydroxy-5-cyanopyrid-6-one, 1,4-dimethyl-5-carbamoylpyrid-6-one, 2,6-dihydroxy-4-ethyl-5-cyanopyridine, 2-hydroxy-4-ethyl-5-carbamoylpyrid-6-one or 1-methyl-2-hydroxy-4-methylsulfonylpyrid-6-one.

Examples of suitable coupling components of the barbituric acid series are barbituric acid, dimethylbarbituric acid and diethylbarbituric acid.

Examples of pyrazolone coupling components are 3-methyl- or 3-($C_1$–$C_4$-alkoxycarbonyl)pyrazol-5-ones which can carry, in position 1, hydrogen or unsubstituted or methyl, ethyl, flouro-, chloro-, bromo-, methoxy-, ethoxy-, cyano-, acetylamino-, hydroxy-, carbamoyl- or sulfamoyl-substituted phenyl. By way of example, mention may be made of 1-(2',5'-dichlorophenyl)-3-methylpyrazol-5-one, ethyl 1-phenylpyrazol-5-one-3-carboxylate, and ethyl pyrazol-5-one-3-carboxylate.

Preference is given to dyes of the formula I in which $R^1$ is hydrogen.

Preference is also given to dyes of the formula I in which $Q^1$ is hydrogen. Dyes of the formula I in which $Q^1$, $Q^2$ and $Q^3$ independently are hydrogen or $C_1$–$C_4$-alkyl are likewise preferred, particular preference being given to those dyes in which $Q^1$ is hydrogen and $Q^2$ and $Q^3$ independently are $C_1$–$C_4$-alkyl.

Preferred radicals B are $C_2$–$C_6$-alkylene which can be interrupted by oxy or $C_1$–$C_6$-alkylimino. Dyes which include these bridges are likewise preferred.

Preferred coupling components KH are compounds of the formulae IIa and IIb. Particular preference is given to coupling components of the formula IIa in which $R^4$ is hydroxyl, amino, mono- or dimethyl- or -ethylamino or mono- or dihydroxyethylamino, and $R^5$ and $R^6$ independently are hydrogen, hydroxyl, amino or methyl.

Particular preference is likewise given to coupling components of the formula IIb in which $R^7$ is hydroxyl or amino.

The following coupling components are particularly preferred: resorcinol, 3-aminophenol, m-phenylenediamine, α- and β-naphthol, m-toluidine and 2,5-dimethylaniline.

Furthermore, dyes of the formula I in which n is 0 are preferred.

To prepare the dyes of the formula I an amine of the formula III

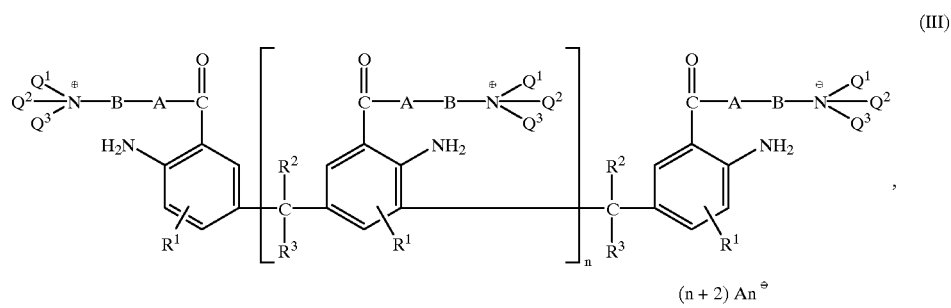

(III)

where n, $R^1$, $R^2$, $R^3$, A, B, $Q^1$, $Q^2$, $Q^3$ and $An^\ominus$ are as defined above can be diazotized by known methods and the products coupled to a coupling component KH. A pH in the range from 5 to 10 is preferably chosen.

The diazonium salt solution is advantageously metered into the solution of the coupling component. It is possible in general to use a single coupling component or mixtures of two or more coupling components in order, for example, to adjust the shade.

By choosing coupling components capable of double coupling it is possible to obtain dyes of relatively high molecular mass, owing to the azo coupling reaction. These oligomeric dyes are obtainable by azo-coupling 1 molar equivalent of amine of the formula III to (n+2)/2 to n+2, preferably to (n+2)/2 to (n+2)/1.5, molar equivalents of a coupling component of the formula IIa'

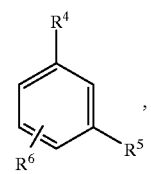

(IIa')

where
  $R^4$ and $R^5$ independently are hydroxyl, amino, morpholino or mono-or di-($C_1$–$C_6$)-alkylamino whose alkyl radicals are unsubstituted or substituted by hydroxyl, amino, cyano, $C_1$–$C_6$-alkoxycarbonyl, carbamoyl or mono- or di-($C_1$–$C_6$)-alkylcarbamoyl and uninterrupted or interrupted by oxy,
  $R^6$ is hydrogen or $C_1$–$C_6$-alkoxy whose alkyl radical is uninterrupted or interrupted by oxy, or is mono- or di-($C_1$–$C_6$)-alkylamino, $C_1$–$C_6$-alkoxycarbonyl, carbamoyl, mono- or di-($C_1$–$C_6$-alkyl)carbamoyl, sulfamoyl, mono- or di-($C_1$–$C_6$-alkyl)sulfamoyl, and n is the number of repeating units of the amine, as defined in formula III.

In analogy to the dyes I, the corresponding amine III is composed of n+2 aminobenzoic acid building blocks.

Preference is given to cationic azo dyes obtainable by azo-coupling 1 molar equivalent of diamine of the formula III' (n=0) to from 1 to 2, preferably 1.5 and, in particular, 1.2 molar equivalents of a coupling component of the formula IIa'. Particular preference is given to azo dyes obtained by the equimolar use of diazo component and coupling component.

The coupling step is conducted at a pH above 5, preferably in a range from 7 to 10. The desired pH can be established and, if necessary, corrected during the coupling reaction by means, for example, of the addition of ammonium bases or alkali metal bases, examples being sodium and potassium hydroxide, carbonate and acetate. Normally, the end point of the reaction is reached no later than 2 hours after the addition of base has ended. Chain termination takes place by coupling to a coupling component no longer possessing a reactive end, or by destroying the diazonium compounds.

The present invention also relates to the abovementioned amines of the formula III which are prepared in the form of their ammonium salts. The amines themselves are of course also embraced by the claims.

Preference is given to amines of the formula III in which $R^1$ is hydrogen.

Likewise preferred are amines of the formula III in which $Q^1$ is hydrogen, and amines of the formula III in which $Q^1$, $Q^2$ and $Q^3$ independently are hydrogen or $C_1$–$C_4$-alkyl, especially those in which $Q^1$ is hydrogen and $Q^2$ and $Q^3$ independently are $C_1$–$C_4$-alkyl.

Furthermore, preference is given to amines of the formula III in which B is $C_2$–$C_6$-alkylene which can be interrupted by oxy or $C_1$–$C_4$-alkylimino.

Preferred amines of the formula III' are those where n=0.

The novel amines of the formula III are obtained by condensing two aromatic compounds of the formula IV

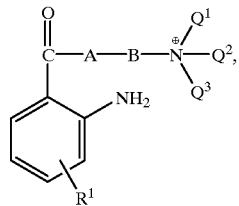

(IV)

where $R^1$, A, B, $Q^1$, $Q^2$, $Q^3$ and $An^\ominus$ are as defined above, with aldehydes and ketones of the formula V

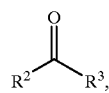

(V)

where $R^2$ and $R^3$ are as defined above, in an acidic medium.

Examples of suitable aldehydes and ketones are formaldehyde, acetaldehyde, propionaldehyde, butyraldehyde, acetone, methyl ethyl ketone and cyclohexanone. It is preferred to employ formaldehyde.

Condensation reactions of this kind on the aromatic nucleus are common knowledge. The two starting compounds are normally reacted at a pH of from 0 to 5 in aqueous solution, for example in a hydrochloric acid medium or sulfuric acid medium. Temperatures from 20 to 70° C. are generally chosen. Depending on the choice of temperature and dilution, the reaction is normally over after from 1 to 6 hours.

The aromatic compounds of the formula (IV) can be condensed on the benzene either para or ortho to the amino group, the para position normally being the more reactive.

Accordingly, through the choice of the molar ratio of the starting compounds in addition to the dimeric amine III where n=0, oligomeric amines III where n>0 are also obtained to an increasing extent if the molar ratio of amine (III) to aldehyde, ketone(V) exceeds 2:1.

Likewise, a temporary excess of aldehyde/ketone(V), as occurs, for example, on rapid addition of the aldehyde/ketone or when the aldehyde/ketone is the initial charge and the amine is added, may lead to a greater amount of oligomers.

If it is intended to prepare the dimers, accordingly, the amine will preferably be introduced initially and the aldehyde/ketone metered into this initial charge. The dimer can be purified by crystallization, for example.

Preferably, however, the mixtures of the dimeric and oligomeric amines are used in the dye synthesis as well, and lead to dye mixtures having advantageous performance properties, in which the individual dyes differ only in their number of repeating units.

If, on the other hand, a molar ratio of amine(III) to aldehyde, ketone(V) of less than 2:1 is chosen in the above-described condensation step, reaction of the product mixture, diazotization and coupling produce dye mixtures which in addition to one or more dyes of the formula I include one or more dyes of the formula (VI)

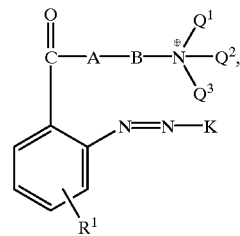

(VI)

where $R^1$, K, A, B, $Q^1$, $Q^2$, $Q^3$ and $An^\ominus$ are as defined above. Dye mixtures obtained in this way are likewise preferred.

The basic azo dyes of the formula I according to the invention can be employed alone, in mixtures with one another, and together with other cationic or anionic compounds in the form of their solutions or in the form of powders or granules. They are suitable advantageously for dyeing or printing polymeric material, especially paper materials such as paper and card, and also cellulose, cotton, leather, bast fibers, hemp, flacks, sizzle, jute, coir, straw or anionically modified fibers, and in recording fluids such as inks, especially for inkjet printing or for printing inks.

In connection with the production of dye preparations comprising the novel dyes of the formula I, emphasis should be placed on the use of polymers, such as polyacrylic acids, polyacrylic acid derivatives, polyvinylamines, polyvinylamides, polyvinyl acetates, polyvinyl alcohols, polyvinylpyrrolidones, polysiloxanes, or copolymers of the respective monomers. It is also possible to employ oligomers of ethyleneimine, ethylene oxide or propylene oxide, or derivatives of these oligomers.

The dyes can preferably be used in connection with the production of pulp-dyed, sized and unsized paper. They can likewise be used for dyeing paper by the dipping process.

Paper, leather or cellulose is dyed in accordance with methods which are known per se.

The novel dyes or preparations thereof cause little or no staining of the papermaking wastewater, which is particularly advantageous in terms of watercourse cleanliness. They are highly substantive, do not marble when applied to paper, and are substantially pH-insensitive. The dyeings on paper are notable for good light fastness. On prolonged exposure to light the shade changes on-tone.

The dyed paper, which is readily bleachable, is wet-fast, not only to water but also to milk, soapy water, sodium chloride solutions, fruit juices or sweetened mineral waters, and, owing to its good alcohol fastness, is also fast to alcoholic beverages.

The novel dyes can also be used for dyeing, padding or printing polyacrylonitrile textiles or anionically modified polyamide or polyester textiles.

The following examples are intended to illustrate the invention.

EXAMPLE A 208.2 g (1 mol) of 2-dimethylaminoethyl 2-aminobenzoate were dissolved in a mixture of 900 ml of water and 70 ml of concentrated sulfuric acid. 41.1 g (0.5 mol) of formaldehyde solution (36.5% strength by weight) were added to this solution over the course of 2 hours at 50° C. after which stirring was continued at 50° C. for a further 4 hours. The mixture was subsequently cooled to 0° C. and adjusted to a pH of 8.0 using 10% strength by weight sodium carbonate solution. Thereafter, the solution was extracted 6 times with 300 ml of methyl tert-butyl ether each time and the combined organic phases were dried over sodium sulfate. Removal of the ether by vacuum distillation gave 138.1 g of crude product as virtually colorless oil. Recrystallization from toluene gave 94.1 g of 6,6'-diaminobis(2-dimethylaminoethyl)-3,3'-methylenebisbenzoate as crystalline pure product.

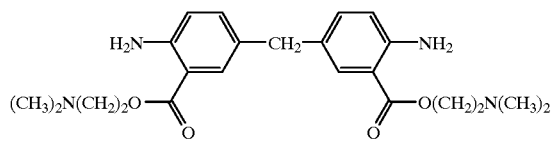

m.p.: 87–89° C. [1] H NMR (CDCl$_3$): δ=2.32 (s, 12 H, CH$_3$), 2.68 (t, 4 H, CH$_2$), 3.75 (s, 2 H, CH$_2$), 4.35 (t, 4 H, CH$_2$), 5.60 (s, 4 H, NH$_2$), 6.60 (d, 2 H, H$_{arom}$), 7.05 (d, 2 H, H$_{arom}$), 7.66 (s, 2 H, H$_{arom}$).

EXAMPLE B 25.2 g (0.1 mol) of 2-(2-dimethylaminoethoxy)ethyl 2-aminobenzoate were dissolved in a mixture of 50 ml of water and 7 ml of concentrated sulfuric acid and then 4.1 g (0.05 mol) of 36.5% strength by weight formaldehyde solution were added dropwise at 50° C. After the end of addition, stirring was continued at 50° C. for a further 4 hours after which the mixture was cooled to 0° C. and adjusted to a pH of 8.0 using 10% strength by weight sodium carbonate solution. The emulsion was subsequently extracted three times with 100 ml of ethyl acetate each time and the organic phases were combined and dried over sodium sulfate. Removal of the ethyl acetate by vacuum distillation gave 15.1 g of 6,6'-diaminobis(2-(2-dimethylaminoethoxy)ethyl)-3,3'-methylenebis benzoate as a pale yellow, viscose oil.

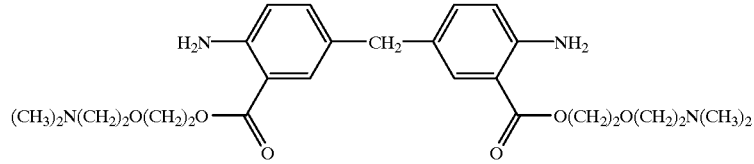

[1] H NMR (CDCl$_3$): δ=2.25 (s, 12 H, CH$_3$), 2.53 (t, 4 H, CH$_2$), 3.63 (t, 4 H, CH$_2$), 3.73 (s, 2 H, CH$_2$), 3.80 (t, 4 H, CH$_2$), 4.40 (t, 4 H, CH$_2$), 5.60 (s, 4 H, NH$_2$), 6.56 (d, 2 H, H$_{arom}$), 7.03 (d, 2 H, H$_{arom}$). 7.70 (s, 2 H, H$_{arom}$).

EXAMPLE C 20.7 g of 2-amino-N-(2-dimethylaminoethyl)benzamide were dissolved in a mixture of 90 ml of water and 7 ml of concentrated sulfuric acid, the solution was heated to 50° C., and 4.1 g of 36.5% strength by weight formaldehyde solution were added dropwise to this solution at 50° C. over the course of 15 minutes. The mixture was subsequently stirred at 50° C. for a further 4 hours and cooled to room temperature and the solution was adjusted to a pH of 9 using 10% strength by weight sodium hydroxide solution. The product separated out as an oil and was separated from the water phase in a separating funnel. The vacuum drying gave 21.5 g of 6,6'-diamino-N,N'-bis(2-dimethylaminoethyl)-3,3'-methylenebis-benzamide as a substance which undergoes glasslike solidification.

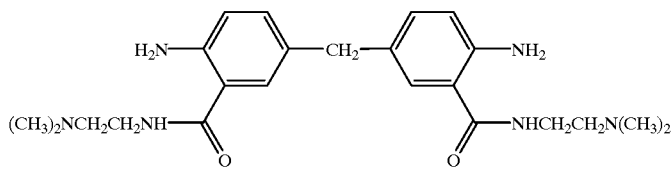

m.p.(toluene): $^1$H NMR (CDCl$_3$): δ=2.22 (s, 12 H, CH$_3$), 2.46 (t, 4 H, CH$_2$), 3.44 (t, 4 H, CH$_2$), 3.71 (s, 2 H, CH$_2$), 5.42 (s, 4 H, NH$_2$), 6.57 (d, 2 H, H$_{arom}$), 6.97 (d, 2 H, H$_{arom}$), 7.15 (s, 2 H, H$_{arom}$).

EXAMPLE 1

4.3 g (0.01 mol) of 6,6'-diaminobis(2-dimethylaminoethyl)-3,3'-methylenebisbenzoate (as prepared in Example A) were dissolved in 50 ml of water and 6 ml of concentrated hydrochloric acid, and 6.6 ml of sodium nitrite solution (23% strength) were added slowly to the solution at from 0 to 5° C. The mixture was subsequently stirred at from 0 to 5° C. for 45 minutes and then excess nitrite was destroyed by adding sulfamic acid. The diazonium salt solution was then added dropwise to a solution of 2.2 g of resorcinol in 200 ml of water. At the same time, a pH of from 9.5 to 10.0 was established by adding 10% strength by weight sodium hydroxide solution and the temperature was held at 0° C. by adding ice. After the end of addition, stirring was continued at 0° C. for 10 minutes at a pH of 10 and then a pH of 7.2 was established at 0° C. with concentrated hydrochloric acid. The mixture was subsequently left to warm to room temperature overnight. The resultant orange-red precipitate was filtered off with suction, washed with water and dried under reduced pressure at 60° C. to give 6.2 g of a dye of the formula

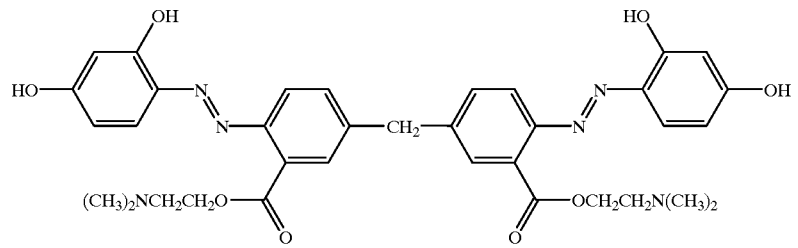

λ$_{max}$ (dilute acetic acid): 402 nm

In accordance with the procedure of Example 1 it is possible to prepare dyes having good light fastness properties from 6,6'-diaminobis(2-dimethylaminoethyl)-3,3'-methylenebisbenzoate as diazo component and the coupling components listed in Table 1 below:

TABLE 1

| Example No. | Coupling component | λ$_{max}$ of dye (in dilute acetic acid) |
|---|---|---|
| 1.1 | | 472 nm |
| 1.2 | | 496 nm |
| 1.3 | ![](3-hydroxy-2-naphthoic acid) | 500 nm |
| 1.4 | ![](methyl 3-hydroxy-2-naphthoate) | 504 nm |

TABLE 1-continued

| Example No. | Coupling component | λ$_{max}$ of dye (in dilute acetic acid) |
|---|---|---|
| 1.5 | | 522 nm |

TABLE 1-continued

| Example No. | Coupling component | λ_max of dye (in dilute acetic acid) |
|---|---|---|
| 1.6 | 3-hydroxy-2-naphthamide with NHCH₂CH₂NH₂ | 522 nm |
| 1.7 | 3-hydroxy-2-naphthamide with NHCH₂CH₂OH | 504 nm |
| 1.8 | 3-methylaniline | 502 nm |
| 1.9 | 2,4-dimethylaniline | 506 nm |
| 1.10 | N,N-diethylaniline | 514 nm |
| 1.11 | N,N-bis(2-hydroxyethyl)aniline | 532 nm |
| 1.12 | 1,3-phenylenediamine | 468 nm |
| 1.13 | 4-methyl-3-cyano-2,6-dihydroxypyridine | 442 nm |
| 1.14 | 1-methyl-3-(4-methyl-2,6-dihydroxypyridin-3-yl)pyrrolium | 436 nm |
| 1.15 | 6-hydroxy-2,4(1H,3H)-pyrimidinedione | 402 nm |
| 1.16 | 3-methyl-5-pyrazolone | 418 nm |
| 1.17 | 3-(N,N-diethylamino)phenol | 482 nm |
| 1.18 | N-ethyl-2-naphthylamine | 510 nm |
| 1.19 | N-ethyl-1-naphthylamine | 544 nm |

Likewise in accordance with the procedure of Example 1 it is possible to obtain dyes having good performance properties by diazotizing and coupling 6,6'-diaminobis(2-(2-dimethylaminoethoxy)ethyl)-3,3'-methylene-bisbenzoate (Example B) or 6,6'-diamino-N,N'-bis(2-dimethylaminoethyl)-3,3'-methylenebis-benzamide (Example C).

EXAMPLE 2

20.8 g (0.1 mol) of 2-dimethylaminoethyl 2-aminobenzoate were dissolved in a mixture of 90 ml of water and 7 ml of concentrated sulfuric acid. 4.1 g (0.05 mol) of 36.5% strength by weight formaldehyde solution were added to the aforementioned solution over the course of 30 minutes at 50° C. and the mixture was subsequently stirred at 50° C. for 4 hours more. It was then cooled to 0° C., after which the first 20.4 g (11.5 ml) of concentrated sulfuric acid and then, at from 0 to 5° C., 30 ml of 23% strength by weight sodium nitrite solution were added. The mixture was stirred for half an hour more at from 0 to 5° C. and then excess nitrite was destroyed by adding sulfamic acid.

The diazonium salt solution was added dropwise to the solution of 12.1 g of resorcinol in 150 ml of water. In the course of this procedure a pH of 9.0 was established by simultaneous metered addition of 10% strength by weight sodium hydroxide solution, the temperature being held at 0° C. After the end of the addition the mixture was stirred at 0° C. and a pH of 9.0 for 10 minutes more and then adjusted to a pH of 7.2 using 10% strength by weight sulfuric acid at 0° C. The mixture was then left to warm to room temperature overnight, after which the resulting reddish brown precipitate was filtered off with suction. The precipitate was washed and dried under reduced pressure at 60° C. to give 32.6 g of a dye mixture comprising the dye described in Example 1 as the principal component and trimeric and oligomeric derivatives (see Example 3) as secondary components.

$\lambda_{max}$ (dilute acetic acid): 400 nm

EXAMPLE 3

20.8 g (0.1 mol) of 2-dimethylaminoethyl 2-aminobenzoate were dissolved in a mixture of 90 ml of water and 7 ml of concentrated sulfuric acid. 9.0 g (0.1 mol) of 36.5% strength by weight formaldehyde solution were added to the aforementioned solution over the course of 30 minutes at 50° C. and the mixture was subsequently stirred at 50° C. for 4 hours more. It was then cooled to 0° C., after which the first 20.4 g (11.5 ml) of concentrated sulfuric acid and then, at from 0 to 5° C., 30 ml of 23% strength by weight sodium nitrite solution were added. The mixture was stirred for half an hour more at from 0 to 5° C. and then excess nitrite was destroyed by adding sulfamic acid.

The diazonium salt solution was added dropwise to the solution of 12.1 g of resorcinol in 150 ml of water. In the course of this procedure a pH of 9.0 was established by simultaneous metered addition of 10% strength by weight sodium hydroxide solution, the temperature being held at 0° C. by adding ice. After the end of the addition the mixture was stirred at 0° C. and pH of 9.0 for 10 minutes more and then adjusted to a pH of 7.2 using 10% strength by weight sulfuric acid at 0° C. The mixture was then left to warm to room temperature overnight, after which the resulting reddish brown precipitate was filtered off with suction. The precipitate was washed with water and dried under reduced pressure at 60° C. to give 31.5 g of a mixture of oligomeric dyes of the formula

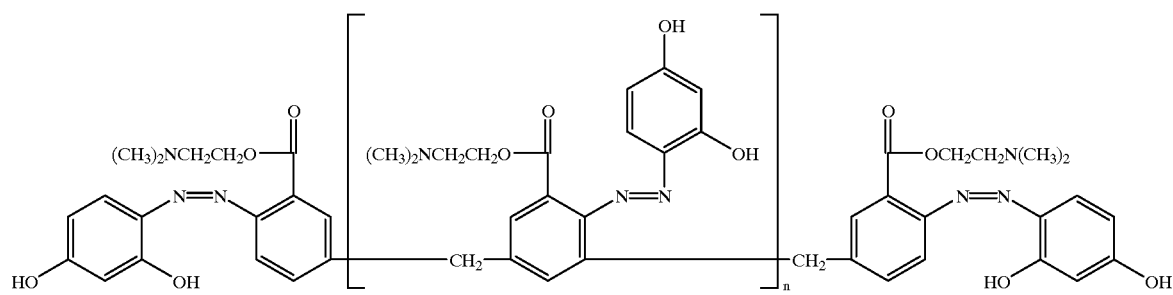

$\lambda_{max}$ (dilute acetic acid): 404 nm

In accordance with the procedure of Example 3 it is possible to prepare the dyes listed in Table 2.

TABLE 2

| Example No. | Coupling component | $\lambda_{max}$ (in dilute acetic acid) |
|---|---|---|
| 2.1 | 3-hydroxy-2-naphthoic acid N-(2-aminoethyl)amide | 506 nm |
| 2.2 | 4-methyl-3-cyano-6-hydroxy-2-pyridone | 436 nm |
| 2.3 | 1-methyl-3-(4-methyl-6-hydroxy-2-pyridon-3-yl)pyrrole | 428 nm |

EXAMPLE 4

In accordance with the procedure of Example 2, 20.8 g (0.1 mol) of 2-dimethylaminoethyl 2-aminobenzoate were reacted with 4.1 g (0.05 mol) of 36.5% strength by weight formaldehyde solution, the reaction product was diazotized and the diazonium salt solution was coupled to 6.1 g (0.055 mol) of resorcinol to give 27.5 g of an oligomeric dye mixture whose absorption maximum $\lambda_{max}$ (in dilute acetic acid) is 432 nm.

EXAMPLE 5

20.8 g of 2-dimethylaminoethyl 2-aminobenzoate were dissolved in a mixture of 90 ml of water and 7 ml of concentrated sulfuric acid. 2.0 g of 36.5% strength by weight formaldehyde solution were added to the aforementioned solution over the course of 30 minutes at 50° C. and the mixture was subsequently stirred at 50° C. for 4 hours more. It was then cooled to 0° C., after which the first 20.4 g (11.5 ml) of concentrated sulfuric acid and then, at from 0 to 5° C., 30 ml of 23% strength by weight sodium nitrite solution were added. The mixture was stirred for half an hour more at from 0 to 5° C. and then excess nitrite was destroyed by adding sulfamic acid.

The diazonium salt solution was added dropwise to the solution of 12.1 g of resorcinol in 150 ml of water. In the course of this procedure a pH of 9.0 was established by simultaneous metered addition of 10% strength by weight sodium hydroxide solution, the temperature being held at 0° C. by adding ice. After the end of the addition the mixture was stirred at 0° C. and pH of 9.0 for 10 minutes more and then adjusted to a pH of 7.2 using 10% strength by weight sulfuric acid at 0° C. The mixture was then left to warm to room temperature overnight, after which the resulting orange precipitate was filtered off with suction. The precipitate was washed with water and dried under reduced pressure at 60° C. to give 33.5 g of a dye mixture consisting of the dyes of the formulae

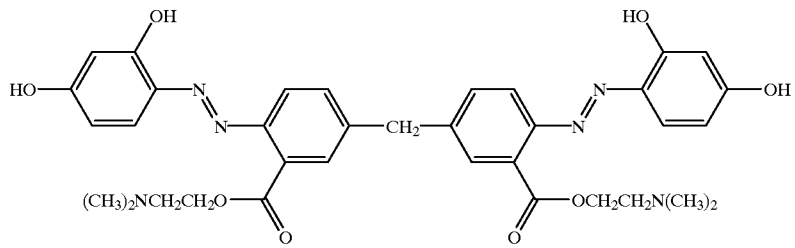

and

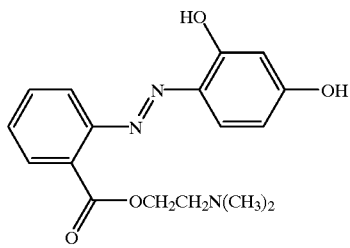

also trimeric and tetrameric derivatives, as described in Example 3, where n=1 and 2, as secondary components. The dye mixture has an absorption maximum $\lambda_{max}$ (in dilute acetic acid) of 396 nm.

We claim:

1. A cationic azo dye of the formula I

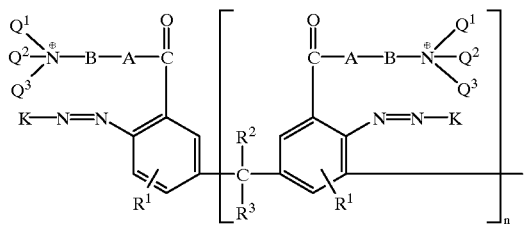

-continued

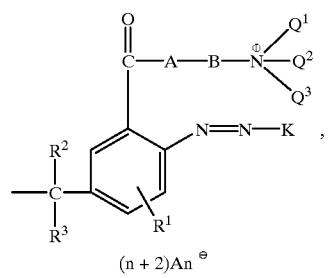

where
n is a number from 0 to 8,
$R^1$ is hydrogen, nitro, halogen or $C_1$–$C_6$-alkyl,
$R^2$ and $R^3$ are independently hydrogen or $C_1$–$C_6$-alkyl or together with the carbon atom linking them are a cyclopentyl or cyclohexyl radical,
K is the radical of a coupling component,
A is oxy, imino or unsubstituted or substituted $C_1$–$C_6$-alkylimino,
B is $C_1$–$C_6$-alkylene which may be interrupted by 1 or 2 nonadjacent oxy, imino or unsubstituted or substituted $C_1$–$C_6$-alkylimino groups and a radical

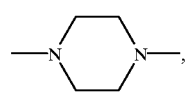

$Q^1$, $Q^2$ and $Q^3$ independently are hydrogen, $C_1$–$C_{10}$-alkyl which may be interrupted by from 1 to 4 nonadjacent oxy, imino and unsubstituted or substituted $C_1$–$C_4$-alkylimino groups and may be substituted by hydroxyl, halogen or phenyl, and $Q^1$ and $Q^2$ together with the nitrogen atom linking them are a 5- or 6-membered heterocyclic radical with or without nitrogen or oxygen as a further heteroatom, and
$An^\ominus$ is the equivalent of an anion.

2. A dye as claimed in claim 1, wherein K is the radical of a coupling component from the benzene, naphthalene, quinoline, pyridone, barbituric acid or pyrazolone series.

3. A dye as claimed in claim 1, wherein B is $C_2$–$C_6$-alkylene which may be interrupted by oxy or $C_1$–$C_6$-alkylimino.

4. A cationic azo dye obtainable by azo-coupling 1 molar equivalent of amine of the formula III

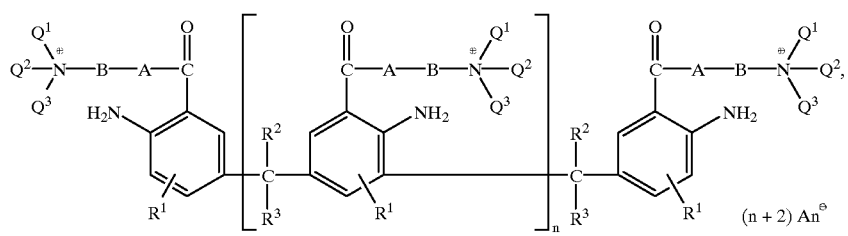

where n, $R^1$, $R^2$, $R^3$, A, B, $Q^1$, $Q^2$, $Q^3$ and $An^\ominus$ are as defined in claim 1, to (n+2)/2 to n+2 molar equivalents of a coupling component of the formula IIa'

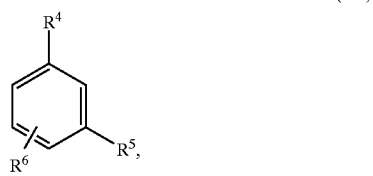

where $R^4$ and $R^5$ independently of one another are hydroxyl, amino, morpholino or mono- or di-($C_1$–$C_6$)-alkylamino whose alkyl radicals are unsubstituted or substituted by hydroxyl, amino, cyano, $C_1$–$C_6$-alkoxycarbonyl, carbamoyl or mono- or di-($C_1$–$C_6$)-alkylcarbamoyl and uninterrupted or interrupted by oxy, $R^6$ is hydrogen or $C_1$–$C_6$-alkoxy whose alkyl radical is uninterrupted or interrupted by oxy, or is mono-or di-($C_1$–$C_6$)-alkylamino, $C_1$–$C_6$-alkoxycarbonyl, carbamoyl, mono- or di-($C_1$–$C_6$-alkyl)carbamoyl, sulfamoyl, mono- or di-($C_1$–$C_6$-alkyl)sulfamoyl.

5. A cationic azo dye obtainable by azo-coupling 1 molar equivalent of diamine of the formula III'(n=0) to from 1 to 2 molar equivalents of a coupling component of the formula IIa'.

6. A process for preparing a dye as claimed in claim 4 by coupling 1 molar equivalent of amine to (n+2)/2 to n+2 molar equivalents of a coupling component of the formula IIa'.

7. An amine of the formula III

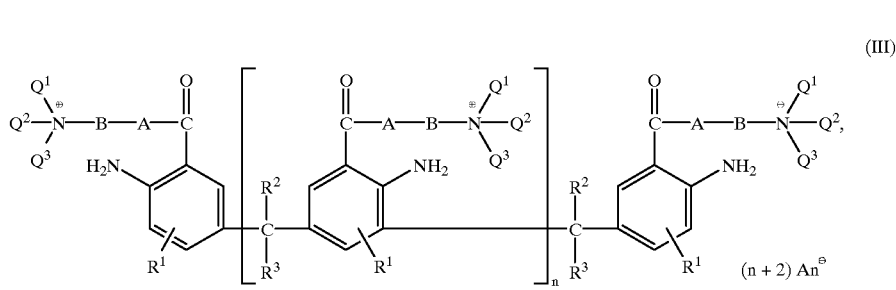

where n, $R^1$, $R^2$, $R^3$, A, B, $Q^1$, $Q^2$, $Q^3$ and $An^\ominus$ are as defined in claim 1.

8. A dye mixture comprising two or more dyes of the formula I as claimed in claim 1 which differ in their number of repeating units.

9. A dye mixture comprising one or more dyes of the formula I as claimed in claim 1 and also one or more dyes of the formula VI (VI)

where $R^1$, K, A, B, $Q^1$, $Q^2$, $Q^3$ and $An^\ominus$ are as defined in claim 1.

10. A method of dyeing or printing polymeric materials comprising applying thereto a cationic azo dye or mixture of such dyes as claimed in claim 1.

* * * * *